United States Patent [19]
Scozzari

[11] Patent Number: 6,069,243
[45] Date of Patent: May 30, 2000

[54] PROCESS FOR OLIGONUCLEOTIDE SYNTHESIS

[75] Inventor: Anthony Scozzari, Vista, Calif.

[73] Assignee: Isis Pharmaceuticals, Inc., Carlsbad, Calif.

[21] Appl. No.: 09/167,165

[22] Filed: Oct. 6, 1998

[51] Int. Cl.⁷ .......................... C07H 21/00; C07H 21/02; C07H 21/04
[52] U.S. Cl. .......................................................... 536/25.34
[58] Field of Search .......................................... 536/25.34

[56] References Cited

U.S. PATENT DOCUMENTS

| | | | |
|---|---|---|---|
| Re. 34,069 | 9/1992 | Köster et al. | 536/25.34 |
| 4,415,732 | 11/1983 | Caruthers et al. | 536/26.5 |
| 4,458,066 | 7/1984 | Caruthers et al. | 536/25.34 |
| 4,500,707 | 2/1985 | Caruthers et al. | 536/25.34 |
| 4,517,338 | 5/1985 | Urdea et al. | 525/54 |
| 4,668,777 | 5/1987 | Caruthers et al. | 536/26.5 |
| 4,725,677 | 2/1988 | Köster et al. | 536/25.34 |
| 4,973,679 | 11/1990 | Caruthers et al. | 536/26.71 |
| 5,034,506 | 7/1991 | Summerton et al. | 528/391 |
| 5,132,418 | 7/1992 | Caruthers et al. | 536/25.3 |
| 5,138,045 | 8/1992 | Cook et al. | 536/24.5 |
| 5,151,510 | 9/1992 | Stec et al. | 536/25.34 |
| 5,210,264 | 5/1993 | Yau | 558/167 |
| 5,218,105 | 6/1993 | Cook et al. | 536/25.31 |
| 5,292,875 | 3/1994 | Stec et al. | 536/25.33 |
| 5,440,068 | 8/1995 | Blackman et al. | 558/435 |
| 5,459,255 | 10/1995 | Cook et al. | 536/27.13 |
| 5,539,082 | 7/1996 | Nielsen et al. | 530/300 |
| 5,571,902 | 11/1996 | Ravikumar et al. | 536/22.1 |
| 5,889,136 | 3/1999 | Scaringe et al. | 536/25.34 |
| 5,902,881 | 5/1999 | Cheruvallath et al. | 536/25.3 |

FOREIGN PATENT DOCUMENTS

WO 92/20823  11/1992  WIPO .

OTHER PUBLICATIONS

Alul, R.H. et al., "Oxalyl–CPG: a labile support for synthesis of sensitive oligonucleotide derivatives", *Nuc. Acid Res.*, 1991, 19, 1527–1532 (Iss. No. 7).

Berner, S. et al., "Studies on the role of tetrazole in the activation of phosphoramidites", *Nucl. Acids. Res.*, 1989, 17, 853–864 (Issue No. 3).

Crooke, S.T. et al., "Pharmacokinetic Properties of Several Novel Oligonucleotide Analogs in mice", *J. Pharmacol. Exp. Therapeutics*, 1996, 277, 923–937 (Iss. No. 2).

Dahl, O. et al., "Preparation of Nucleoside Phosphorothioates, Phosphorodithioates and Related Compounds", *Sulfur Reports*, 1991, 11(1), 167–192.

Dahl, B.H. et al., "Mechanistic studies on the phosphoramidite coupling reaction in oligonucleotide synthesis. I. Evidence for nucleophilic catalysis by tetrazole and rate variations with the phosphorus substituents", *Nucl. Acids Res.*, 1987, 15, 1729–1743(#4).

Eckstein, F., "Nucleoside Phosphorothioates", *Ann. Rev. Biochem.*, 1985, 54, 367–402.

Efimov, V.A. et al., "New efficient sulfurizing reagents for the preparation of oligodeoxyribonucleotide phosphorothioate analogues", *Nucl. Acids Res.*, 1995, 23, 4029–4033 (Issue No. 20).

Gait, M.S., *Oligonucleotide Synthesis: A Practical Approach*, IRL Press, 1984, 18–22.

Gebeyehu, G. et al., "Novel bitinylated nucleotide—analogs for labeling and colorimetric detection of DNA", *Nucl. Acids Res.*, 1987, 15, 4513–4534 (Iss. No. 11).

Iyer, R.P. et al., "The Automated Synthesis of Sulfur–Containing Oligodeoxyribonucleotides Using 3H–1,2–Benzodithiol–3–one 1,1–Dioxide as a Sulfur–Transfer Reagent", *J. Org. Chem.*, 1990, 55, 4693–4699 (Issue No. 15).

Iyer, R.P. et al., "3H–1,2–Benzodithiole–3–one 1,1–Dioxide as an Improved Sulfurizing Reagent in the Solid–Phase Synthesis of Oligodeoxyribonucleoside Phosphorothioates", *J. Am. Chem. Soc.*, 1990, 112, 1253–1254.

Kabanov, A.V.,"A new class of antivirals: antisense olgonucleotides combined with a hydrophobic substituent effectively inhibit influenza virus reproduction and synthesis of virus–specific proteins in MDCK cells", *FEBS Letts.*, 1990, 259, 327–330 (Jan., 1990).

Kamer, P.C.J. et al., "An Efficient Approach Toward the Synthesis of Phosphorothioate Diesters via the Schonberg Reaction", *Tetrahedron Letts.*, 1989, 30, 6757–6760 (Issue No. 48).

Kornberg, A., *DNA Replication*, W.H. Freeman and Co., San Francisco, 1980, 75–77.

Kresse, J. et al., "The use of S–2–cyanoethyl phosphorothioate in the preparation of oligo 5'–deoxy–5'–thiothymidylates", *Nucl. Acids Res.*, 1975, 2, 1–9(Jan. '75, Iss. No.

Letsinger, R.L. et al., "Cholesteryl–conjugated oligonucleotides: Synthesis, properties and activity as inhibitors of replication of human immunodeficiency virus in cell culture", *Proc. Natl. Acad. Sci.*, 1989, 86, 6553–6556 (Sep., 1989).

Manoharan, M. et al., "Chemical Modifications to Improve Uptake and Bioavailability of Antisense Oligonucleotides", *Annals NY Acad. Sciences*, 1992, 660, 306–309.

(List continued on next page.)

Primary Examiner—Cecilia Tsang
Assistant Examiner—L. Eric Crane
Attorney, Agent, or Firm—Woodcock Washburn Kurtz MacKiewicz & Norris LLP

[57] ABSTRACT

The present invention describes methods for linking phosphoramidite nucleosides to a solid support-bound nucleoside. This invention presents novel processes for synthesizing oligonucleotides. Acetonitrile having a water content between 30 ppm and about 1250 ppm is used as the solvent for the washing steps in solid phase oligonucleotide synthesis, or is used as a solvent for the capping reagent or oxidizing reagent. The processes of the present invention are amenable to large-scale, economic oligonucleotide synthesis using the phosphoramidite method.

17 Claims, No Drawings

OTHER PUBLICATIONS

Manoharan, M. et al., "Introduction of a Lipophilic Thioether Tether in the Minor Groove of Nucleic Acids for Antisense Applications", *Bioorg. Med. Chem. Letts.*, 1993, 3, 2765–2770 (Issue No. 12).

Manoharan M. et al., "Cholic Acid–Oligonucliotide Conjugates for Antisense Applications", *Bioorganic Med. Chem. Letts.*, 1994, 4, 1053–1060 (Iss. No. 8).

Manoharan, M. et al., "Lipidic Nucleic Acids", *Tetrahedron Letts.*, 1995, 36, 3651–3654 (Issue No. 2).

Manoharan M. et al., "Oligonucleotide Conjugates: Alteration of the Pharmacokinetic Properties of Antisense Agents", *Nucleosides and Nucleotides*, 1995, 14, 969–973 (#3–5).

Martin, P., "Ein neuer Zugang zu 2'–O–Alkylribonucleosiden und Eigenschaften deren Oligonucleotide", *Helvetica Chemica Acta*, 1995, 78, 486–504.

Mishra, R.K. et al., "Improved leishmanicidal effect of phosphorotioate antisense oligonucleotides by LDL–medicated delivery", *Biochim. Et Biophysica*, 1995, 1264, 229–237.

Nielsen, J. et al., "Thermal Instability of Some Alkyl Phosphorodiamidites", *J. Chem. Res.*, 1986, S, 26–27.

Nielsen, P.E. et al., "Sequence–Selective Recognition of DNA by Strand Displacement with a Thymine–Substituted Polyamide", *Science*, 1991, 254, 1497–1500 (Dec. 6, 1991).

Oberhauser, B. et al., "Effective incorporation of 2'–O–methyl–oligonucleotides into liposomes and enhanced cell association through modification with thiocholesterol", *Nucl. Acids Res.*, 1992, 20, 533–538 (Issue No. 3).

Rao, M.V. et al., "Dibenzoyl Tetrasulphide–A Rapid Sulphur Transfer Agent in the Synthesis of Phosphorothioate Analogues of Oligonucleotides", *Tetrahedron Letts.*, 1992, 33, 4839–4842 (Issue No. 33).

Saison–Behmoaras, T. et al., "Short modified antisense oligonucleotides directed against Ha–ras point mutation induce selective cleavage of the mRNA and inhibit T24 cells proliferation", *EMBO J.*, 1991, 10, 1111–1118 (Issue No. 5).

Sekine, M et al., "Synthesis and Properties of S,S–Diaryl Nucleoside Phosphorodithioates in Oligonucleotide Synthesis", *J. Org. Chem.*, 1979, 44(13), 2325–2326.

Shea, R.G. et al., "Synthesis, hybridization properties and antiviral activity of lipid–oligodeoxynucleotide conjugates", *Nucl. Acids Res.*, 1990, 18, 3777–3783 (Iss. No. 13).

Svinarchuk, F.P. et al., "Inhibition of HIV proliferation in MT–4 cells by antisense oligonucleotide conjugated to lipophilic groups", *Biochimie*, 1993, 79, 49–54.

Vu, H. et al., "Internucleotide Phosphite Sulfurization with Tetraethylthiuram Disulfide. Phosphorothioate Oligonucleotide Synthesis via Phosphoramidite Chemistry", *Tetrahedron Letts.*, 1991, 32, 3005–3008 (Iss. No. 26).

Wright, P. et al., "Large Scale Synthesis of Oligonucleotides via phosphoramidite Nucleosides and a High–loaded Polystyrene Support", *Tetrahedron Letts.*, 1993, 34, 3373–3376 (Issue No. 21).

Xu, Q. et al., "Efficient introduction of phosphorothioates into RNA oligonucleotides by 3–ethoxy–1,2, 4–dithiazoline–5–one (EDITH)", *Nucl. Acids Res.*, 1996, 24, 3643–3644 (Issue No. 18).

Xu, Q. et al., "Use of 1,2,4–dithiazolidine (DtsNH) and 3–ethoxy–1,2,4–dithiazoline–5–one (EDITH) for synthesis of phosphorothioate–containing oligodeoxyribonucleotides", *Nucl. Acids Res.*, 1996, 24, 1602–1607 (Issue No. 9).

Yau, E.K. et al., "Synthesis of Dinucleoside and Dinucleotide Phosphorodithioates Via a Phosphotriester Approach", *Tetrahedron Letts.*, 1990, 31, 1953–1956 (Iss. No. 14).

PROCESS FOR OLIGONUCLEOTIDE SYNTHESIS

FIELD OF THE INVENTION

This invention relates to an improved process for coupling a phosphoramidite nucleoside to a solid support-bound nucleoside. The present invention is useful for the synthesis of oligonucleotides. This invention is amenable to large-scale synthesis of oligonucleotides using the phosphoramidite method.

BACKGROUND OF THE INVENTION

Oligonucleotides and their analogs are routinely used in many diagnostic and research applications, as probes, primers, linkers, adaptors and antisense oligonucleotides. Antisense oligonucleotides have been used routinely in research to study the functions of gene products, i.e. proteins, by modulating the expression thereof. These oligonucleotides are designed to bind in a specific fashion to a particular mRNA sequence by hybridization (i.e., oligonucleotides that are specifically hybridizable with a target mRNA). Such oligonucleotides and oligonucleotide analogs are intended to inhibit the activity of the selected mRNA by any of a number of mechanisms, i.e., to interfere with translation reactions by which proteins coded by the mRNA are produced or initiate RNase H degradation of the mRNA. The inhibition of the formation of the specific proteins that are coded for by the mRNA sequences allows the study of functions of certain genes.

The specificity of antisense oligonucleotides and their analogs suggests that they might be useful therapeutically. Their mechanism of action should limit side effects while increasing specificity. Presently, there are numerous antisense oligonucleotides in clinical trials against a wide range of targets and diseases and recently the first antisense oligonucleotide was approved by the FDA for marketing.

Applications of oligonucleotides and oligonucleotide analogs as antisense agents for therapeutic purposes, diagnostic purposes, and research reagents often require that the oligonucleotides or oligonucleotide analogs be synthesized in large quantities. This is especially true for their use as commercially available pharmaceutical drugs. The large-scale synthesis of oligonucleotides on an economic scale presents different challenges than those in synthesis of small amounts for research.

Synthesis of oligonucleotides can be accomplished using both solution phase and solid phase methods. A general review of solid-phase versus solution-phase oligonucleotide synthesis is given in the background section of Urdea et al. U.S. Pat. No. 4,517,338, entitled "Multiple Reactor System And Method For Oligonucleotide Synthesis". Oligonucleotide synthesis via solution phase can be accomplished with several coupling mechanisms.

One such solution phase preparation utilizes phosphorus triesters. Yau, E. K. el al., *Tetrahedron Letters,* 1990, 31, 1953, report the use of phosphorous triesters to prepare thymidine dinucleoside and thymidine dinucleotide phosphorodithioates. However, solution phase chemistry requires purification after each internucleotide coupling, which is labor-intensive and time-consuming.

Further details of methods useful for preparing oligonucleotides may be found in Sekine, M. et. al., *J. Org. Chem.,* 1979, 44, 2325; Dahl, O., *Sulfer Reports,* 1991, 11, 167–192; Kresse, J. et al., *Nucleic Acids Res.,* 1975, 2, 1–9; Eckstein, F., *Ann. Rev. Biochem.,* 1985, 54, 367–402; and Yau, E. K. U.S. Pat. No. 5,210,264.

The current method of choice for the preparation of naturally-occurring oligonucleotides, as well as oligonucleotides with modified internucleotide linkages such as phosphorothioate and phosphoro-dithioate oligonucleotides, is via solid-phase synthesis. Solid-phase synthesis involves the attachment of a nucleoside to a solid support, such as a polymer support, and the addition of a second nucleotide onto the support-bound nucleotide. Further nucleotides are added, thus forming an oligonucleotide which is bound to a solid support. The oligonucleotide can then be cleaved from the solid support when synthesis of the desired length and sequence of oligonucleotide is achieved.

Solid-phase synthesis relies on sequential addition of nucleotides to one end of a growing oligonucleotide chain. Typically, a first nucleoside, having protecting groups on any exocyclic amine functionalities present, is attached to an appropriate solid support. Activated phosphorus compounds, typically nucleotide phosphoramidites, also bearing appropriate protecting groups, are added step-wise to elongate the growing oligonucleotide. The activated phosphorus compounds are reacted with the growing oligonucleotide using "fluidized bed" technology to mix the reagents.

A number of solid-phase synthesizers are available commercially. These are suitable for preparing relatively small quantities of oligonucleotides, i.e., from about the micromolar ($\mu$mol) to millimolar (mmol) range. They typically are not amenable to the preparation of the larger quantities of oligonucleotides necessary for biophysical studies, pre-clinical and clinical trials and commercial production due to the high cost of reagents.

Instruments for large-scale solid phase synthesis of oligonucleotides are also commercially available, for example, the Pharmacia OligoPilot II and Milligen/Biosearch 8800. Although the process used by these machines is well understood, they require use of expensive reagents. Given the vast amounts of oligonucleotide syntheses performed for research use and for large scale manufacture pursuant to clinical trials, any waste of these expensive reagents is a significant economic problem.

One reagent used in large quantities is acetonitrile, which is used in multiple washing steps, as a solvent for an activator during the coupling step of the phosphoramidite method, and as a solvent for phosphoramidites, capping solution and an oxidation reagent. It is accepted dogma by those skilled in the art that "low water content" acetonitrile, i.e. having a water content less than 30 ppm, is mandatory for oligonucleotide synthesis. See, in general, Gait, M. S., *Oligonucleotide Synthesis A Practical Approach*, IRL Press 1985, p. 18–19. It is believed that using acetonitrile with a greater water content during any of the synthesis steps results in sub-optimal yields. The presence of water in the system is thought to interfere with the coupling reaction. Consequently, costly low water content acetonitrile is universally used for oligonucleotide synthesis. "Reagent grade" acetonitrile, acetonitrile having a water content higher than 30 ppm is available, but the process of removing water and other impurities from such reagent grade acetonitrile is costly and lengthy. See, U.S. Pat. No. 5,440,068 for a review of the art.

Thus there remains a need for improved and more economical processes for oligonucleotide synthesis.

SUMMARY OF THE INVENTION

The present invention is directed to improved processes for linking a phosphoramidite nucleoside to a solid support-bound nucleoside. The present invention further encompasses the synthesis of oligonucleotides. This invention is based on the finding that oligonucleotide synthesis efficiency, as measured by coupling efficiency and percent full length, need not be significantly diminished when substituting acetonitrile with water content greater than 30 ppm and less than 1250 ppm for low water acetonitrile in the washing steps of the synthesis process, or as a solvent for capping reagents or as a solvent for a number of oxidation/sulfurization reagents. This invention embodies methods of solid-phase oligonucleotide synthesis comprising coupling a phosphoramidite nucleoside to a reactive hydroxyl group of a nucleoside bound to a solid-phase support. This is preferably done in the presence of an activating reagent, thereby forming a phosphorus linkage between the two nucleosides; capping any uncoupled deprotected support-bound nucleoside with a capping reagent; and oxidizing the phosphorus nucleoside linkage with an oxidizing reagent. The solid support is washed with acetonitrile prior to or subsequent to at least one of the coupling, capping and oxidizing reactions, said acetonitrile having a water content of greater than 30 ppm and less than about 1250 ppm. Alternatively, at least one of the capping reagent or oxidizing reagent is in an acetonitrile solvent having a water content of greater than 30 ppm and less than about 1250 ppm. The improved processes described herein provide means for more economical syntheses of oligonucleotides.

DETAILED DESCRIPTION OF THE PREFERRED EMBODIMENTS

The present invention is directed to methods for linking a phosphoramidite nucleoside to a solid support-bound nucleoside. These methods comprise attaching a first nucleoside having a protected hydroxyl group to a solid support by means of a covalent linkage. The first nucleoside may be attached to the solid support either directly or via a linker, using standard methods and procedures known in the art. See, e.g., *Oligonucleotides and Analogues: A Practical Approach*, Eckstein, F, Ed., IRL Press, New York, 1991, hereby incorporated by reference in its entirety. One example is a long chain alkylamine linker incorporating a carbamate linkage. The attached protected nucleoside is then deprotected with a deprotecting reagent and coupled with a second phosphoramidite nucleoside to form a phosphorus nucleoside linkage between the first nucleoside and the second nucleoside. This coupling occurs at the hydroxyl group, of the first nucleoside, which becomes reactive upon deprotection with the deprotecting reagent. Following this coupling step, the remaining deprotected but uncoupled first nucleoside is optionally capped with a capping reagent. The resultant phosphorus nucleoside linkage is next oxidized with an oxidizing agent. According to the methods of the present invention, during the linking of a phosphoramidite nucleoside to a solid support-bound nucleoside, the solid support is washed with acetonitrile prior to or subsequent to at least one of the coupling, capping or oxidizing steps, wherein the acetonitrile has a water content between 30 ppm and about 1250 ppm, or at least one of the capping or oxidizing reagents is in an acetonitrile solvent having a water content of between 30 ppm and about 1250 ppm.

In a preferred embodiment the solid support is washed with acetonitrile prior to or subsequent to at least one of the coupling, capping or oxidizing steps, wherein the acetonitrile has a water content between 30 ppm and about 1250 ppm, and at least one of the capping or oxidizing reagents is in an acetonitrile solvent having a water content of between 30 ppm and about 1250 ppm.

In another preferred embodiment the solid support is washed with acetonitrile prior to or subsequent to at least one of the coupling, capping or oxidizing steps, wherein the acetonitrile has a water content between 30 ppm and about 1250 ppm, and the capping and oxidizing reagents are in an acetonitrile solvent having a water content of between 30 ppm and about 1250 ppm.

In another preferred embodiment the water content of the acetonitrile is between 30 ppm and 400 ppm. It is further preferred that the water content be between 30 ppm and 200 ppm. In a still further preferred embodiment the water content is between 200 ppm and 400 ppm.

Methods for synthesizing oligonucleotides include conversion of a nucleoside or nucleobase to an activated phosphorus compound followed by solution phase or solid phase chemistries to couple the activated phosphorus compound to a growing oligonucleotide chain. Solution and solid phase chemistries typically involve a multi-step reaction cycle which is repeated for each addition of the activated phosphorus compound. Representative solution phase techniques are described in U.S. Pat. Nos. 5,210,264 and 5,571,902, both herein incorporated by reference. Representative solid phase techniques are those typically employed for DNA and RNA synthesis utilizing standard phosphoramidite chemistry. See, e.g., *Protocols For Oligonucleotide And Analogs*, Agrawal, S., ed., Humana Press, Totowa, N.J., 1993. A typical solid-phase reaction cycle for using phosphoramidites includes the following steps: washing the solid support, detritylating, which deprotects the sugar moiety, washing, coupling of a phosphoramidite monomer to the detritylated nucleoside, washing, capping of unreacted/uncoupled support bound phosphoramidite monomer, washing, oxidizing the phosphorus nucleoside linkage, and washing. See, e.g., *Oligonucleotides and Analogues: A Practical Approach*, Eckstein, F. Ed., IRL Press, New York, 1991. Oxidation may follow capping and is depicted in Scheme 1 along with all the washing steps.

SCHEME 1

Synthesis Cycle

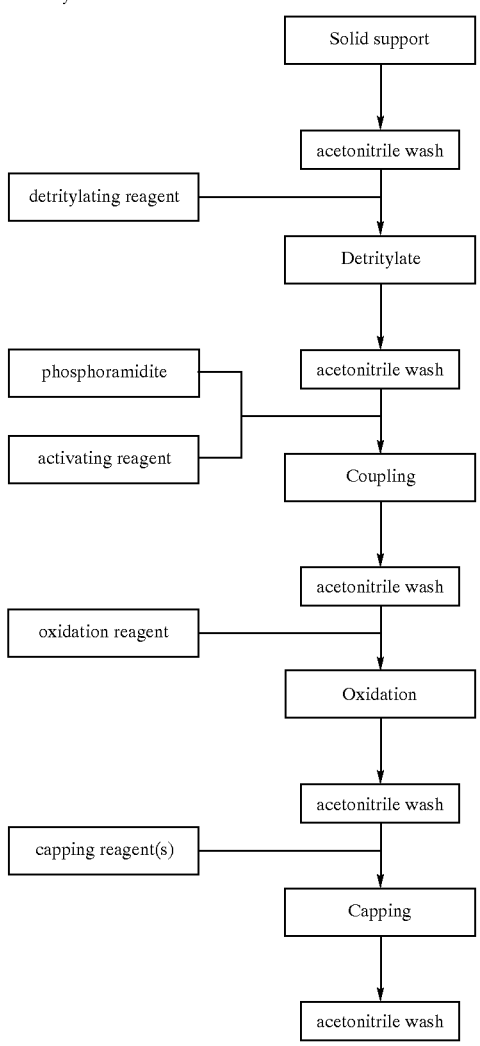

The present invention also provides methods for the synthesis of an oligonucleotide comprising the steps of attaching a first protected nucleoside to a solid support by means of a covalent linkage. The first nucleoside may be attached to the solid support either directly or via a linker, using standard methods and procedures known in the art. See, e.g., *Oligonucleotide and Analogues: A Practical Approach*, Eckstein, F, Ed., IRL Press, New York, 1991, hereby incorporated by reference in its entirety. The attaching step is then followed by deprotecting the hydroxyl group to reveal a reactive hydroxyl group. This is followed by coupling a second phosphoramidite to the reactive hydroxyl group of the first nucleoside to form a phosphorus nucleoside linkage, capping any remaining uncoupled but deprotected first nucleoside, and oxidizing the phosphorus nucleoside linkage with an oxidizing reagent. The deprotecting, coupling, capping and oxidizing steps are repeated iteratively until an oligonucleotide of desired sequence and length is formed. According to the methods of the present invention, during the synthesis of an oligonucleotide, the solid support is washed with acetonitrile prior to or subsequent to at least one of the coupling, capping or oxidizing steps, wherein the acetonitrile has a water content between 30 ppm and about 1250 ppm, or at least one of the capping or oxidizing reagents is in an acetonitrile solvent having a water content of between 30 ppm and about 1250 ppm.

In a preferred embodiment the solid support is washed with acetonitrile prior to or subsequent to at least one of the coupling, capping or oxidizing steps, wherein the acetonitrile has a water content between 30 ppm and about 1250 ppm, and at least one of the capping or oxidizing reagents is in an acetonitrile solvent having a water content of between 30 ppm and about 1250 ppm.

In another preferred embodiment the solid support is washed with acetonitrile prior to or subsequent to at least one of the coupling, capping or oxidizing steps, wherein the acetonitrile has a water content between 30 ppm and about 1250 ppm, and the capping and oxidizing reagents are in an acetonitrile solvent having a water content of between 30 ppm and about 1250 ppm.

In a further embodiment of the present invention it is preferred that the water content of the acetonitrile be between 30 ppm and 400 ppm. It is further preferred that the water content be between 30 ppm and 200 ppm. In a still further preferred embodiment the water content is between 200 ppm and 400 ppm.

It has universally been believed that low water acetonitrile must be used throughout the oligonucleotide synthesis process. The present invention provides methods of using acetonitrile having a water content greater than 30 ppm but less than 1250 ppm during the washing steps of oligonucleotide synthesis or as a solvent for a capping solution or as a solvent for an oxidation/sulfurization agent. Great savings in time and expense are attained thereby.

In solid support synthesis, the deprotected 5'-hydroxyl of the support-bound nucleoside, or growing oligonucleotide chain, is reacted with a 5'-protected activated phosphoramidite nucleoside to produce a covalent linkage between the support-bound nucleoside and the phosphoramidite nucleoside. The activated phosphorus compound is one that is known to undergo a coupling reaction with the deprotected 5'-hydroxyl of a growing oligomeric chain according to standard synthetic methodologies, such as, for example, the phosphoramidite, phosphotriester and H-phosphonate synthetic methods. See, e.g., Caruthers U.S. Pat. Nos. 4,415,732; 4,458,066; 4,500,707; 4,668,777; 4,973,679; and 5,132,418; Yau, E. K. U.S. Pat. No. 5,210,264; and Koster U.S. Pat. Nos. 4,725,677 and Re. 34,069; each of the disclosures of which are hereby incorporated by reference in their entirety, Sekine, M. et al., *J. Org. Chem.,* 1979, 44, 2325; Dahl, O., *Sulfur Reports,* 1991, 11, 167–192; Kresse, J. et al., *Nucleic Acids Res.,* 1975, 2, 1–9; Eckstein, F., *Ann. Rev. Biochem.,* 1985, 54, 367–402; and *Oligonucleotides and Analogues A Practical Approach*, Eckstein, F. Ed., IRL Press, New York, 1991.

Any activating agent, or activator, that can activate the phosphorous to nucleophilic attack without interacting with the growing nucleotide chain may be suitable for use with the present invention. Such agents are commonly mild acid catalysts. One preferred activating agent is tetrazole. Some commonly used commercially available activating agents are thiotetrazole, nitrotetrazole, and N,N-diisopropylaminohydrotetrazolide. Other suitable activating agents are also disclosed in the above incorporated patents as well as in U.S. Pat. No. 4,725,677 herein incorporated by reference, and in Berner, S. et al., *Nucleic Acids Res.* 1989, 17:853; Dahl, B. H. et al., *Nucleic Acids Res.* 1987, 15:1729; and Nielsen, J. et al., *Chem. Res., Synop.* 1986, 1, 26–27.

In some preferred embodiments, an oxidation of the phosphite linkage to a phosphodiester linkage is performed after each deprotection-coupling cycle. Useful oxidizing agents for producing phosphodiester oligonucleotides include iodine and t-butyl hydroperoxide.

Alternatively, oxidation with sulfurizing agents is used to form phosphorothioate linkages. These include Beaucage reagent (see, e.g., Iyer, R. P. et al., *J. Chem. Soc.*, 1990, 112, 1253–1254, and Iyer, R. P. et al., *J. Org. Chem.*, 1990, 55, 4693–4699); tetraethylthiuram disulfide (see e.g., Vu, H. and Hirschbein, B. L., *Tetrahedron Lett.*, 1991, 32, 3005–3008); dibenzoyl tetrasulfide (see, e.g., Rao, M. V. et al., *Tetrahedron Lett.*, 1992, 33, 4839–4842); di(phenylacetyl)disulfide (PADS) (see, e.g., Kamer, P. C. J., *Tetrahedron Lett.*, 1989, 30, 6757–6760); 1,2,4-dithiuazoline-5-one (DtsNH) and 3-ethoxy-1,2,4-dithiuazoline-5-one (EDITH) and (see Xu et al., *Nucleic Acids Research*, 1996, 24, 3643–3644 and Xu et al., *Nucleic Acids Research*, 1996, 24, 1602–1607); thiophosphorus compounds such as those disclosed in U.S. Pat. No. 5,292,875 to Stec et al., and U.S. Pat. No. 5,151,510 to Stec et al., especially bis(O,O-diisopropoxy phosphinothioyl) disulfide, disulfides of sulfonic acids, such as those disclosed in Efimov et al., *Nucleic Acids Research*, 1995, 23, 4029–4033, sulfur, sulfur in combination with ligands like triaryl, trialkyl, triaralkyl, or trialkaryl phosphines. Preferred oxidation/sulfurization agents for this invention include iodine, t-butyl hydroperoxide and PADS.

Capping reagents include commercially available solutions designated for such purposes. The capping step prevents unreacted support bound phosphoramidite monomer from reacting at a later step. A common set of capping reagents is an acetic anhydride solution in acetonitrile and a 4-methylaminopyridine solution in tetrahydrofuran (THF). Acetonitrile may also be used in place of THF as a solvent for 4-methylaminopyridine. Most other capping reagents used are derivatives of acetic anhydride. For example, when phenoxyacetyl is used as a protecting group for exocyclic amines, phenyl acetic anhydride is used as a capping agent.

Solid supports used in solid-phase oligonucleotide synthesis include controlled pore glass (CPG), oxalyl-controlled pore glass (see, e.g., Alul et al., *Nucleic Acids Research* 1991, 19, 1527), TentaGel Support—an aminopolyethyleneglycol derivatized support (see, e.g., Wright et al., *Tetrahedron Letters* 1993, 34, 3373), Poros—a copolymer of polystyrene/divinylbenzene or PRIMER SUPPORT® HL, 30—a polystyrene based support (Pharmacia Biotech, Piscataway, N.J.). Preferred solid supports amenable to this invention include those that are hydrophobic. Preferred embodiments of the invention utilize polystyrene based solid supports. Many other solid supports are commercially available and amenable to the present invention.

It is recognized that the equivalents of phosphoramidite may vary. Equivalents is defined as the molar ratio of phosphoramidites to loading of the solid support. Phosphoramidites are known to act as a drying agent. Thus, by using higher equivalents of phosphoramidites, higher quantities of water may be present in the acetonitrile used in the invention. For example, at 2.5 equivalents, acetonitrile with a water content greater than 30 ppm and less than 1250 ppm may be used. Preferred is the use of acetonitrile with a water content between 30 ppm and 1000 ppm. At 2.5 equivalents, acetonitrile with a water content between 30 ppm and 850 ppm may be used. Preferred is the use of acetonitrile with a water content between 30 ppm and 600 ppm. At 1.75 equivalents, acetonitrile with a water content between 30 ppm and 650 ppm may be used. Preferred is the use of acetonitrile with a water content between 30 ppm and 400 ppm. At 1.5 equivalents, acetonitrile with a water content greater than 30 ppm and less than 1250 ppm may be used.

Preferred is the use of acetonitrile with a water content between 30 ppm and 1000 ppm. Based on this information, feasible water content for acetonitrile to be used with other equivalents may be determined.

The methods of the invention are amenable to the well-known technique of solid phase synthesis. Equipment for such synthesis is sold by several vendors including Applied Biosystems, Pharmacia, and Milligen. Both the Applied Biosystems and Milligen systems utilize an upright reaction vessel for holding the solid support. Solvents are pumped into the vessel and mixed with the solid support. An inert gas, typically, argon, is used to remove solvents rapidly. Such instruments use a fluidized-bed technology. Instruments such as the OligoPilot II, sold by Pharmacia, use a flow-through reactor, similar in concept to column chromatography. Use of instruments that utilize a flow-through reactor are preferred. Any other means for such synthesis may also be employed; the actual synthesis of the oligonucleotides is well within the talents of the routineer.

It is well known to use similar techniques to prepare oligonucleotides incorporating phosphorothioate linkages and oligonucleotides incorporating 2'-alkoxy or 2'-alkoxyalkoxy modifications, including 2'-O-methoxyethyl (Martin, P., *Helv. Chim. Acta* 1995, 78, 486). It is also well known to use similar techniques and commercially available modified phosphoramidites such as biotin, fluorescein, acridine or psoralen-modified phosphoramidites (available from Glen Research, Sterling, Va.) to synthesize fluorescently labeled, biotinylated or other conjugated oligonucleotides.

In a preferred embodiment of the invention, acetonitrile having a water content greater than 30 ppm and less than 1250 ppm is purchased from commercial sources and used as-is. Acetonitrile of such quality is readily available from many vendors, including J. T. Baker (Phillipsburg, N.J.), and may be labeled as HPLC quality. In other embodiments of the invention, low water acetonitrile may be recycled after use. Typically, after oligonucleotide synthesis, the acetonitrile is discarded. It is believed that the acetonitrile will contain too much water to be useful. The invention disclosed herein supports the use of recycled acetonitrile containing a water content greater than 30 ppm.

In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

Specific examples of preferred modified oligonucleotides include those containing phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioates (abbreviated as P=S) and those with $CH_2$—NH—O—$CH_2$, $CH_2$—N($CH_3$)—O—$CH_2$ [known as a methylene(methylimino) or MMI backbone], $CH_2$—O—N($CH_3$)—$CH_2$, $CH_2$—N($CH_3$)—N($CH_3$)—$CH_2$ and O—N($CH_3$)—$CH_2$—$CH_2$ backbones, wherein the native phosphodiester (abbreviated as P=O) backbone is represented as O—P—O—$CH_2$. Also preferred are oligonucleotides having morpholino backbone structures (Summerton and Weller, U.S. Pat. No. 5,034,506). Further preferred are oligonucleotides with NR—C(*)—CH$_2$—CH$_2$, CH$_2$—NR—C(*)—CH$_2$, CH$_2$—CH$_2$—NR—C(*), C(*)—NR—CH$_2$—CH$_2$ and CH$_2$—C(*)—NR—CH$_2$ backbones, wherein "*" represents O or S (known as amide backbones; DeMesmaeker et al., WO 92/20823, published Nov. 26, 1992). In other preferred embodiments, such as the peptide nucleic acid (PNA) backbone, the phosphodiester backbone of the oligonucleotide is replaced with a polyamide backbone, the nucleobases being bound directly or indirectly to the aza nitrogen atoms of the polyamide backbone (Nielsen et al., Science 1991, 254, 1497; U.S. Pat. No. 5,539,082). Other preferred modified oligonucleotides may contain one or more substituted sugar moieties comprising one of the following at the 2'position. OH, SH, SCH$_3$, F, OCN, OCH$_3$OCH$_3$, OCH$_3$O(CH$_2$)$_n$CH$_3$, O(CH$_2$)$_n$NH$_2$ or O(CH$_2$)$_n$CH$_3$ where n is from 1 to about 10; O—R or O—R—O—R where R is C$_1$ to C$_{10}$ lower alkyl, substituted lower alkyl, alkaryl or aralkyl; O-substituted lower alkyl, Cl; Br; CN; CF$_3$; OCF$_3$; O—, S—, or N-alkyl; O—, S—, or N-alkenyl; SOCH$_3$; SO$_2$CH$_3$; ONO$_2$; NO$_2$; N$_3$; NH$_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-O-methoxyethyl [which can be written as 2'-O—CH$_2$CH$_2$OCH$_3$, and is also known as 2'-O-(2-methoxyethyl) or 2'-methoxyethoxy] (Martin et al., Helv. Chim. Acta 1995, 78, 486). Other preferred modifications include 2'-methoxy (2'-O—CH$_3$), 2'-propoxy (2'-OCH$_2$CH$_2$CH$_3$) and 2'-fluoro (2'-F). Similar modifications may also be made at other positions on the oligonucleotide, particularly the 3' position of the sugar on the 3' terminal nucleotide and the 5' position of the 5' terminal nucleotide. Oligonucleotides may also have sugar mimetics such as cyclobutyls in place of the pentofuranosyl group.

The oligonucleotides made by the invention may additionally or alternatively include nucleobase modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine and 5-methylcytosine, as well as synthetic nucleobases, e.g., 5-bromouracil, 5-hydroxymethyluracil, 8-azaguanine, 7-deazaguanine, N$^6$(6-aminohexyl)adenine and 2,6-diaminopurine (Kornberg, A., DNA Replication, W. H. Freeman & Co., San Francisco, 1974, pp. 75–77; Gebeyehu, G. et al., Nucleic Acids Res. 1987, 15, 4513). 5-methylcytosine (5-me-C) is presently a preferred nucleobase, particularly in combination with 2'-O-methoxyethyl modifications.

Another preferred additional or alternative modification of the oligonucleotides prepared according to the methods of the invention involves chemically linking to the oligonucleotide one or more lipophilic moieties which enhance the cellular uptake of the oligonucleotide. Such lipophilic moieties may be linked to an oligonucleotide at several different positions on the oligonucleotide. Some preferred positions include the 3' position of the sugar of the 3' terminal nucleotide, the 5' position of the sugar of the 5' terminal nucleotide, and the 2' position of the sugar of any nucleotide. The N$^6$ position of a purine nucleobase may also be utilized to link a lipophilic moiety to an oligonucleotide of the invention (Gebeyehu, G. et al., Nucleic Acids Res. 1987, 15, 4513). Such lipophilic moieties include but are not limited to a cholesteryl moiety (Letsinger et al., Proc. Natl. Acad. Sci. USA 1989, 86, 6553), cholic acid (Manoharan et al., Bioorg Med. Chem. Let. 1994, 4, 1053), a thioether, e.g., hexyl-S-tritylthiol (Manoharan et al., Ann. N.Y. Acad. Sci. 1992, 660, 306; Manoharan et al., Bioorg. Med. Chem. Let. 1993, 3, 2765), a thiocholesterol (Oberhauser et al., Nucl Acids Res. 1992, 20, 533), an aliphatic chain, e.g., dodecandiol or undecyl residues (Saison-Behmoaras et al., EMBO J. 1991, 10, 111; Kabanov et al., FEBS Lett. 1990, 259, 327; Svinarchuk et al., Biochimie 1993, 75, 49), a phospholipid, e.g., di-hexadecyl-rac-glycerol or triethylammonium 1,2-di-O-hexadecyl-rac-glycero-3-H-phosphonate (Manoharan et al., Tetrahedron Lett. 1995, 36, 3651; Shea et al., Nucl. Acids Res. 1990, 18, 3777), a polyamine or a polyethylene glycol chain (Manoharan et al., Nucleosides & Nucleotides 1995, 14, 969), or adamantane acetic acid (Manoharan et al., Tetrahedron Lett. 1995, 36, 3651), a palmityl moiety (Mishra et al., Biochim. Biophys. Acta 1995, 1264, 229), or an octadecylamine or hexylamino-carbonyl-oxycholesterol moiety (Crooke et al., J. Pharmacol. Exp. Ther. 1996, 277, 923). Oligonucleotides comprising lipophilic moieties, and methods for preparing such oligonucleotides, as disclosed in U.S. Pat. Nos. 5,138,045, 5,218,105 and 5,459,255, the contents of which are hereby incorporated by reference.

Oligonucleotides which are chimeric oligonucleotides may also be prepared according to the methods of the present invention. "Chimeric" oligonucleotides, or "chimeras," in the context of this invention, are oligonucleotides which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Cleavage of the RNA target can be routinely detected by gel electrophoresis and, if necessary, associated nucleic acid hybridization techniques.

Examples of chimeric oligonucleotides include but are not limited to "gapmers," in which three distinct regions are present, normally with a central region flanked by two regions which are chemically equivalent to each other but distinct from the gap. A preferred example of a gapmer is an oligonucleotide in which a central portion (the "gap") of the oligonucleotide serves as a substrate for RNase H and is preferably composed of 2'-deoxynucleotides, while the flanking portions (the 5' and 3' "wings") are modified to have greater affinity for the target RNA molecule but are unable to support nuclease activity (e.g., 2'-fluoro- or 2'-O-methoxyethyl- substituted). Other chimeras include "wingmers," also known as "hemimers," that is, oligonucleotides with two distinct regions. In a preferred example of a wingmer, the 5' portion of the oligonucleotide serves as a substrate for RNase H and is preferably composed of 2'-deoxynucleotides, whereas the 3' portion is modified in such a fashion so as to have greater affinity for the target RNA molecule but is unable to support nuclease activity (e.g., 2'-fluoro- or 2'-O-methoxyethyl- substituted), or viceversa. In one embodiment, the oligonucleotides of the present invention contain a 2'-O-methoxyethyl (2'-O—CH$_2$CH$_2$OCH$_3$) modification on the sugar moiety of at least one nucleotide. This modification has been shown to increase both affinity of the oligonucleotide for its target and nuclease resistance of the oligonucleotide. According to the invention, one, a plurality, or all of the nucleotide subunits of the oligonucleotides of the invention may bear a 2'-O-methoxyethyl (—O—CH$_2$CH$_2$OCH$_3$) modification. Oligonucleotides comprising a plurality of nucleotide subunits having a 2'-O-methoxyethyl modification can have such a modification on any of the nucleotide subunits within the oligonucleotide, and may be chimeric oligonucleotides. Aside from or in addition to 2'-O-methoxyethyl modifications, oligonucleotides containing other modifications which enhance antisense efficacy, potency or target affinity are also preferred. Chimeric oligonucleotides comprising one or more such modifications are presently preferred. Oligonucleotides prepared in accordance with the methods of this invention are from 5 to 50 nucleotides in length. In the context of this invention it is understood that this encompasses non-naturally-occurring oligomers as hereinbefore described, having from 5 to 50 monomers.

EXAMPLES

Example 1

Preparation of Acetonitrile

To low water acetonitrile, various quantities of distilled water were added, calculated to give acetonitrile with water contents of 200, 400 and 1200 ppm. Actual water content was measured using the Karl Fisher method. Acetonitrile with water contents of 243, 396 and 650 ppm was obtained.

Example 2

Synthesis of Fully-modified 5'-d(TCC-CGC-CTG-TGA-CAT-GCA-TT)-3' Phosphorotliloate Oligonucleotide with 243 ppm Acetonitrile The synthesis of the above sequence was performed on a Pharmacia OligoPilot II Synthesizer, using standard conditions, on a 175 mmole scale using the cyanoethyl phosphoramidites (Amersham Pharmacia Biotech, Piscataway, N.J.) and Pharmacia's PRIMER SUPPORT® HL, 30. Amidite solutions were made up in low water acetonitrile. 1.75 equivalents of phosphoramidite were used. Detritylation was performed using 3% dichloroacetic acid in toluene (volume/volume). Sulfurization was performed using a 0.2 M solution of phenylacetyl disulfide in 243 ppm acetonitrile:3-picoline (1:1 v/v) for 2 minutes. Acetonitrile containing 243 ppm water was used for washing and as a solvent of the capping reagents. Low water acetonitrile was used as a solvent for tetrazol. At the end of synthesis, the support was washed with acetonitrile, cleaved, deprotected and purified in the usual manner (*Protocols for Oligonucleotides and Analogs*, Agrawal, S., ed., Humana Press, New Jersey 1993, 33–61).

Example 3

Synthesis of Fully-modified 5'-d(TCC-CGC-CTG-TGA-CAT-GCA-TT)-3' Phosphorothioate Oligonucleotide with 396 ppm Acetonitrile The synthesis of the above sequence was performed on a Pharmacia OligoPilot II Synthesizer on a 175 mmole scale using the cyanoethyl phosphoramidites and Pharmacia's PRIMER SUPPORT® HL, 30. Amidite solutions were made up in low water acetonitrile. 1.75 equivalents of phosphoramidite were used. Detritylation was performed using 3% dichloroacetic acid in toluene (volume/volume). Sulfurization was performed using a 0.2 M solution of phenylacetyl disulfide in 396 ppm acetonitrile:3-picoline (1:1 v/v) for 2 minutes. Acetonitrile containing 396 ppm water was used for washing and as a solvent of the capping reagents. Low water acetonitrile was used as a solvent for tetrazol. At the end of synthesis, the support was washed with acetonitrile, cleaved, deprotected and purified in the usual manner.

Example 4

Synthesis of Fully-modified 5'-d(TCC-CGC-CTG-TGA-CAT-GCA-TT)-3' Phosphorothioate Oligonucleotide with 650 ppm Acetonitrile The synthesis of the above sequence was performed on a Pharmacia OligoPilot II Synthesizer on a 175 mmole scale using the cyanoethyl phosphoramidites and Pharmacia's PRIMER SUPPORT® HL, 30. Amidite solutions were made up in low water acetonitrile. 1.75 equivalents of phosphoramidite were used. Detritylation was performed using 3% dichloroacetic acid in toluene (volume/volume). Sulfurization was performed using a 0.2 M solution of phenylacetyl disulfide in 650 ppm acetonitrile:3-picoline (1:1 v/v) for 2 minutes. Acetonitrile containing 650 ppm water was used for washing and as a solvent of the capping reagents. Low water acetonitrile was used as a solvent for tetrazol. At the end of synthesis, the support was washed with acetonitrile, cleaved, deprotected and purified in the usual manner.

Example 5

Synthesis of Fully-modified 5'-d(GCC-CAA-GCT-GGC-ATC-CGT-CA)-3' Phosphorothioate Oligonucleotide with 243 ppm Acetonitrile The synthesis of the above sequence was performed on a Pharmacia OligoPilot II Synthesizer on a 620 mmole scale using the cyanoethyl phosphoramidites and Pharmacia's PRIMER SUPPORT® HL, 30. Amidite solutions were made up in low water acetonitrile. 1.75 equivalents of phosphoramidite were used. Detritylation was performed using 3% dichloroacetic acid in toluene (volume/volume). Sulfurization was performed using a 0.2 M solution of phenylacetyl disulfide in 243 ppm acetonitrile:3-picoline (1:1 v/v) for 2 minutes. Acetonitrile containing 243 ppm water was used for washing and as a solvent of the capping reagents. Low water acetonitrile was used as a solvent for tetrazol. At the end of synthesis, the support was washed with acetonitrile, cleaved, deprotected and purified in the usual manner.

Example 6

Synthesis of Fully-modified 5'-d(GCC-CAA-GCT-GGC-ATC-CGT-CA)-3' Phosphorothioate Oligonucleotide with 396 ppm Acetonitrile The synthesis of the above sequence was performed on a Pharmacia OligoPilot II Synthesizer on a 620 mmole scale using the cyanoethyl phosphoramidites and Pharmacia's PRIMER SUPPORT® HL, 30. Amidite solutions were made up in low water acetonitrile. 1.75 equivalents of phosphoramidite were used. Detritylation was performed using 3% dichloroacetic acid in toluene (volume/volume). Sulfurization was performed using a 0.2 M solution of phenylacetyl disulfide in 396 ppm acetonitrile:3-picoline (1:1 v/v) for 2 minutes. Acetonitrile containing 396 ppm water was used for washing and as a solvent of the capping reagents. Low water acetonitrile was used as a solvent for tetrazol. At the end of synthesis, the support was washed with acetonitrile, cleaved, deprotected and purified in the usual manner.

Example 7
Synthesis of Fully-modified 5'-d(GCC-CAA-GCT-GGC-ATC-CGT-CA)-3' Phosphorothioate Oligonucleotide with 650 ppm Acetonitrile The synthesis of the above sequence was performed on a Pharmacia OligoPilot II Synthesizer on a 620 mmole scale using the cyanoethyl phosphoramidites and Pharmacia's PRIMER SUPPORT® HL, 30. Amidite solutions were made up in low water acetonitrile. 1.75 equivalents of phosphoramidite were used. Detritylation was performed using 3% dichloroacetic acid in toluene (volume/volume). Sulfurization was performed using a 0.2 M solution of phenylacetyl disulfide in 650 ppm acetonitrile:3-picoline (1:1 v/v) for 2 minutes. Acetonitrile containing 650 ppm water was used for washing and as a solvent of the capping reagents. Low water acetonitrile was used as a solvent for tetrazol. At the end of synthesis, the support was washed with acetonitrile, cleaved, deprotected and purified in the usual manner.

Example 8
Synthesis of Fully-modified 5'-d(GCG-TTT-GCT-CTT-CTT-CTT-GCG)-3' Phosphorothioate Oligonucleotide with 243 ppm Acetonitrile The synthesis of the above sequence was performed on a Pharmacia OligoPilot II Synthesizer on a 620 mmole scale using the cyanoethyl phosphoramidites and Pharmacia's PRIMER SUPPORT® HL, 30. Amidite solutions were made up in low water acetonitrile. 1.75 equivalents of phosphoramidite were used. Detritylation was performed using 3% dichloroacetic acid in toluene (volume/volume). Sulfurization was performed using a 0.2 M solution of phenylacetyl disulfide in 243 ppm acetonitrile:3-picoline (1:1 v/v) for 2 minutes. Acetonitrile containing 243 ppm water was used for washing and as a solvent of the capping reagents. Low water acetonitrile was used as a solvent for tetrazol. At the end of synthesis, the support was washed with acetonitrile, cleaved, deprotected and purified in the usual manner.

Example 9
Synthesis of Fully-modified 5'-d(GCG-TTT-GCT-CTT-CTT-CTT-GCG)-3' Phosphorothioate Oligonucleotide with 396 ppm Acetonitrile The synthesis of the above sequence was performed on a Pharmacia OligoPilot II Synthesizer on a 620 mmole scale using the cyanoethyl phosphoramidites and Pharmacia's PRIMER SUPPORT® HL, 30. Amidite solutions were made up in low water acetonitrile. 1.75 equivalents of phosphoramidite were used. Detritylation was performed using 3% dichloroacetic acid in toluene (volume/volume). Sulfurization was performed using a 0.2 M solution of phenylacetyl disulfide in 396 ppm acetonitrile:3-picoline (1:1 v/v) for 2 minutes. Acetonitrile containing 396 ppm water was used for washing and as a solvent of the capping reagents. Low water acetonitrile was used as a solvent for tetrazol. At the end of synthesis, the support was washed with acetonitrile, cleaved, deprotected and purified in the usual manner.

Example 10
Synthesis of Fully-modified 5'-d(GCG-TTT-GCT-CTT-CTT-CTT-GCG)-3' Phosphorothioate Oligonucleotide with 650 ppm Acetonitrile The synthesis of the above sequence was performed on a Pharmacia OligoPilot II Synthesizer on a 620 mmole scale using the cyanoethyl phosphoramidites and Pharmacia's PRIMER SUPPORT® HL, 30. Amidite solutions were made up in low water acetonitrile. 1.75 equivalents of phosphoramidite were used. Detritylation was performed using 3% dichloroacetic acid in toluene (volume/volume). Sulfurization was performed using a 0.2 M solution of phenylacetyl disulfide in 650 ppm acetonitrile:3-picoline (1:1 v/v) for 2 minutes. Acetonitrile containing 650 ppm water was used for washing and as a solvent of the capping reagents. Low water acetonitrile was used as a solvent for tetrazol. At the end of synthesis, the support was washed with acetonitrile, cleaved, deprotected and purified in the usual manner.

Example 11
Synthesis of Fully-modified 5'-d(GTT-CTC-GCT-GGT-GAG-TTT-CA)-3' Phosphorothioate Oligonucleotide with 243 ppm Acetonitrile The synthesis of the above sequence was performed on a Pharmacia OligoPilot II Synthesizer on a 620 mmole scale using the cyanoethyl phosphoramidites and Pharmacia's PRIMER SUPPORT® HL, 30. Amidite solutions were made up in low water acetonitrile. 1.75 equivalents of phosphoramidite were used. Detritylation was performed using 3% dichloroacetic acid in toluene (volume/volume). Sulfurization was performed using a 0.2 M solution of phenylacetyl disulfide in 243 ppm acetonitrile:3-picoline (1:1 v/v) for 2 minutes. Acetonitrile containing 243 ppm water was used for washing and as a solvent of the capping reagents. Low water acetonitrile was used as a solvent for tetrazol. At the end of synthesis, the support was washed with acetonitrile, cleaved, deprotected and purified in the usual manner.

Example 12
Synthesis of Fully-modified 5'-d(GTT-CTC-GCT-GGT-GAG-TTT-CA)-3' Phosphorothioate Oligonucleotide with 396 ppm Acetonitrile The synthesis of the above sequence was performed on a Pharmacia OligoPilot II Synthesizer on a 620 mmole scale using the cyanoethyl phosphoramidites and Pharmacia's PRIMER SUPPORT® HL, 30. Amidite solutions were made up in low water acetonitrile. 1.75 equivalents of phosphoramidite were used. Detritylation was performed using 3% dichloroacetic acid in toluene (volume/volume). Sulfurization was performed using a 0.2 M solution of phenylacetyl disulfide in 396 ppm acetonitrile:3-picoline (1:1 v/v) for 2 minutes. Acetonitrile containing 396 ppm water was used for washing and as a solvent of the capping reagents. Low water acetonitrile was used as a solvent for tetrazol. At the end of synthesis, the support was washed with acetonitrile, cleaved, deprotected and purified in the usual manner.

Example 13
Synthesis of Fully-modified 15 5'-d(GTT-CTC-GCT-GGT-GAG-TTT-CA)-3' Phosphorothioate Oligonucleotide with 650 ppm Acetonitrile The synthesis of the above sequence was performed on a Pharmacia OligoPilot II Synthesizer on a 620 mmole scale using the cyanoethyl phosphoramidites and Pharmacia's PRIMER SUPPORT® HL, 30. Amidite solutions were made up in low water acetonitrile. 1.75 equivalents of phosphoramidite were used. Detritylation was performed using 3% dichloroacetic acid in toluene (volume/volume). Sulfurization was performed using a 0.2 M solution of phenylacetyl disulfide in 650 ppm acetonitrile:3-picoline (1:1 v/v) for 2 minutes. Acetonitrile containing 650 ppm water was used for washing and as a solvent of the capping reagents. Low water acetonitrile was used as a solvent for tetrazol. At the end of synthesis, the support was washed with acetonitrile, cleaved, deprotected and purified in the usual manner.

Example 14
Efficiency of Oligonucleotide Synthesis Using Acetonitrile with Varying Amounts of Water Content The sequence 5'-TCC-CGC-CTG-TGA-CAT-GCA-TT-3' was synthesized as described in examples 2–4. An additional synthesis was performed essentially as described using low water acetonitrile. Measurements of the quality of the syntheses were obtained as shown in Table 1. All tests performed were as described in *Protocol for Oligonucleotides and Analogs*, Agrawal, S., ed., Humana Press, New Jersey 1993. Full length content was analysed by capillary gel electrophoresis. The ratio of phosphorothioate to phosphodiester (P=S:P=O) was measured by $^{31}$P NMR. Crude yield was measured by UV spectrophotometry.

It is clear that using acetonitrile with a water content between 30 ppm and 400 ppm does not result in reduced efficiency of oligonucleotide synthesis. Using acetonitrile with a water content of 650 ppm resulted in reduced crude yields, but other measures of the quality were not affected.

TABLE 1

Synthesis of TCCCGCCTGTGACATGCATT using Acetonitrile with varying water content

| Water content of acetonitrile | Crude Yield (A260 units/ mmole support) | Crude Full Length (%) | Purified Full Length (%) | Purified n-1 (%) | P=S:P=O |
|---|---|---|---|---|---|
| 30 ppm | 123 | 72 | 89 | 2.1 | 99.3:0.7 |
| 243 ppm | 119 | 73 | 89.1 | 2.4 | 99.5:0.5 |
| 396 ppm | 124 | 73 | 90 | 2.1 | 99.3:0.7 |
| 650 ppm | 104 | 64 | 92 | 2.1 | 99.3:0.7 |

What is claimed is:

1. A method for linking a phosphoramidite nucleoside to a solid support-bound nucleoside comprising the steps of:
   (a) coupling said phosphoramidite nucleoside to a reactive hydroxyl group of said solid support-bound nucleoside to form a phosphorus nucleoside linkage therebetween; and
   (b) oxidizing said phosphorus nucleoside linkage with an oxidizing reagent; wherein said solid support is washed with acetonitrile prior to or subsequent to at least one of said coupling or oxidizing steps, said acetonitrile having a water content between 30 ppm and about 1250 ppm, or said oxidizing reagent is in an acetonitrile solvent having a water content between 30 ppm and about 1250 ppm.

2. The method of claim 1 further comprising the step of capping any of said solid support-bound nucleoside, which may remain uncoupled, with a capping reagent prior to said oxidizing step.

3. The method of claim 1 wherein said water content is between 30 ppm and about 400 ppm.

4. The method of claim 1 wherein said water content is between 30 ppm and about 200 ppm.

5. The method of claim 1 wherein said water content is between about 200 ppm and about 400 ppm.

6. The method of claim 2 wherein at least one of said capping reagent or oxidizing reagent is in an acetonitrile solvent having a water content between 30 ppm and about 1250 ppm.

7. The method of claim 2 wherein said solid support is washed with acetonitrile prior to or subsequent to at least one of said coupling, capping or oxidizing steps, said acetonitrile having a water content between 30 ppm and about 1250 ppm, and the capping reagent and oxidizing reagent are in an acetonitrile solvent having, a water content between 30 ppm and about 1250 ppm.

8. A method for the synthesis of an oligonucleotide comprising the steps of:
   (a) attaching a first nucleoside to a solid support via a covalent linkage;
   (b) coupling a phosphoramidite nucleoside to a reactive hydroxyl group on said first nucleoside to form a phosphorus nucleoside linkage therebetween;
   (c) capping any of said first nucleoside which may remain uncoupled with a capping reagent;
   (d) oxidizing said phosphorus nucleoside linkage with an oxidizing reagent; and
   (e) cleaving said oligonucleotide from said solid support; wherein said solid support is washed with acetonitrile prior to or subsequent to at least one of said coupling, capping or oxidizing steps, said acetonitrile having a water content between 30 ppm and about 1250 ppm, or at least one of said capping, reagent or oxidizing reagent is in an acetonitrile solvent having a water content between 30 ppm and about 1250 ppm.

9. The method of claim 8 further comprising the step of repeating steps (b) to (d) iteratively with subsequent phosphoramidite nucleosides to form an oligonucleotide.

10. The method of claim 8 wherein said solid support is washed with acetonitrile prior to or subsequent to at least one of said coupling, capping or oxidizing steps, said acetonitrile having a water content between 30 ppm and about 1250 ppm, and at least one of said capping reagent or oxidizing reagent is in an acetonitrile solvent having a water content between 30 ppm and about 1250 ppm.

11. The method of claim 8 wherein said solid support is washed with acetonitrile prior to or subsequent to at least one of said coupling, capping or oxidizing steps, said acetonitrile having a water content between 30 ppm and about 1250 ppm, and the capping reagent and oxidizing reagent are in an acetonitrile solvent having a water content between 30 ppm and about 1250 ppm.

12. The method of claim 8 wherein said water content is between 30 ppm and about 400 ppm.

13. The method of claim 8 wherein said water content is between 30 ppm and about 200 ppm.

14. The method of claim 8 wherein said water content is between about 200 ppm and about 400 ppm.

15. The method of claim 8 wherein said solid support is hydrophobic.

16. The method of claim 15 wherein said solid support is polystyrene-based.

17. The method of claim 16 wherein said solid support is packed in a column.

* * * * *

UNITED STATES PATENT AND TRADEMARK OFFICE
CERTIFICATE OF CORRECTION

PATENT NO. : 6,069,243
DATED : May 30, 2000
INVENTOR(S) : Scozzari

It is certified that error appears in the above-identified patent and that said Letters Patent is hereby corrected as shown below:

Column 11,
Line 36, please delete "Phosphorotliloate" and insert therefor -- phosphorothioate -- ;

Column 14,
Line 51, please delete "15" after the word "modified".

Signed and Sealed this

Eighteenth Day of September, 2001

Attest:

NICHOLAS P. GODICI
Attesting Officer  Acting Director of the United States Patent and Trademark Office